(12) United States Patent
Herrmann et al.

(10) Patent No.: US 8,399,499 B2
(45) Date of Patent: Mar. 19, 2013

(54) 3- TO 7-MEMBERED 1,3-DIAZA-4-OXO-HETEROCYCLIC DERIVATIVES CAPABLE OF RELEASING ACTIVE ALDEHYDES OR KETONES

(75) Inventors: Andreas Herrmann, Le Muids (CH); Guillaume Godin, Collonges (FR)

(73) Assignee: Firmenich SA, Geneva (CH)

( * ) Notice: Subject to any disclaimer, the term of this patent is extended or adjusted under 35 U.S.C. 154(b) by 689 days.

(21) Appl. No.: 12/598,153

(22) PCT Filed: Apr. 30, 2008

(86) PCT No.: PCT/IB2008/051668
§ 371 (c)(1),
(2), (4) Date: Oct. 29, 2009

(87) PCT Pub. No.: WO2008/142591
PCT Pub. Date: Nov. 27, 2008

(65) Prior Publication Data
US 2010/0152264 A1    Jun. 17, 2010

(30) Foreign Application Priority Data
May 22, 2007   (WO) .................. PCT/IB2007/051927

(51) Int. Cl.
*A61K 31/4166*   (2006.01)
*C07D 233/32*    (2006.01)

(52) U.S. Cl. .................. 514/386; 548/316.4; 512/10
(58) Field of Classification Search .................. 544/298; 548/316.4; 514/269, 386; 512/10
See application file for complete search history.

(56) References Cited

U.S. PATENT DOCUMENTS
6,037,474 A * 3/2000 Drauz et al. ............... 548/316.4

FOREIGN PATENT DOCUMENTS

| EP | 0 799 885 A1 | 10/1997 |
|---|---|---|
| WO | WO 97/34986 A1 | 9/1997 |
| WO | WO 00/02991 A1 | 1/2000 |
| WO | WO 00/24721 A2 | 5/2000 |
| WO | WO 00/63339 A1 | 10/2000 |
| WO | WO 02/38120 A1 | 5/2002 |

OTHER PUBLICATIONS

Jurcik et al, "Preparation of aminals," Tetrahdron 60 (2004), pp. 3205-3210.*
Pinza et al, J. Med. Chem. (1993), vol. 36, pp. 4214-4220.*
Pinza et al, J. Med. Chem. (1993), vol. 36, pp. 4214-4220.*
International Search Report, application No. PCT/IB2008/051668, mailed Dec. 11, 2008.
Jurëik et al., "Preparation of aminals in water, "Tetrahedron, vol. 60, pp. 3205-3210 (2004).
"Detergents", Ullmann's Encyclopedia of Industrial Chemistry, vol. A8, pp. 315-448 (1987).
"Surfactants", Ullman's Encyclopedia of Industrial Chemistry, vol. A25, pp. 747-817 (1994).

* cited by examiner

*Primary Examiner* — Kamal Saeed
*Assistant Examiner* — Janet L Coppins
(74) *Attorney, Agent, or Firm* — Winston & Strawn LLP

(57) ABSTRACT

The present invention provides 3- to 7-membered 1,3-diaza-4-oxo-heterocyclic derivatives, such as imidazolidinone O derivatives, capable of releasing in a controlled manner a biologically active aldehyde or ketone in the surrounding. The invention also relates to the use of these compounds as perfuming or flavoring ingredients, as well as to the perfuming compositions and consumer articles containing such derivatives. It also provides a process for preparing said derivatives of the invention.

18 Claims, No Drawings

3- TO 7-MEMBERED 1,3-DIAZA-4-OXO-HETEROCYCLIC DERIVATIVES CAPABLE OF RELEASING ACTIVE ALDEHYDES OR KETONES

This application is a 371 filing of International Patent Application PCT/IB2008/051668 filed Apr. 30, 2008.

TECHNICAL FIELD

The present invention provides 3- to 7-membered 1,3-diaza-4-oxo-heterocyclic derivatives capable of releasing in a controlled manner a biologically active aldehyde or ketone into the surrounding. The invention also relates to the use of these compounds as perfuming or flavoring ingredients, as well as to the perfuming compositions and consumer articles containing such derivatives. It also provides a process for preparing said heterocyclic derivatives of the invention.

PRIOR ART

Many active compounds are highly volatile and can thus only be perceived over a limited period of time. Extensive research has therefore been performed in order to find new efficient precursors allowing a controlled release of active volatile molecules, particularly in the field of perfumery and flavoring. The prior art discloses some precursors, which are able to prolong or enhance the effect of active molecules such as fragrances. Nevertheless none of the prior art documents discloses the 1,3-diaza-4-oxo-heterocyclic derivatives of the invention as precursors for the controlled release of aldehydes and ketones.

In WO 00/02991, the reaction of amines with a carbonyl compound to form imines, capable of releasing a perfume, is described. However, the imines formed are difficult to use in liquid applications, due to their relative instability.

V. Jurčík and R. Wilhelm in *Tetrahedron* 2004, 60, 3205-3210, recently reported the preparation of aminals in water. Two different secondary amines and several diamines (giving aminals with 5- to 7-membered rings) are used to synthesize aminals. Nevertheless, the structures of the described compounds are significantly different from the 1,3-diaza-4-oxo-heterocyclic derivatives of the invention and no evidence is provided in that publication for a possible use of these compounds to control the release of volatile active aldehydes and ketones. The article focuses on aminals as synthons for biologically active compounds.

Related structures used as precursors for the controlled release of aldehydes or ketones are also reported in WO 00/24721 and 02/38120 where oxazolidines are described. However, these compounds are very different since the chemical stability and reactivity of ester derivatives are pretty different from the ones of amide derivatives, i.e. of the invention's compounds. Therefore these documents do not anticipate the present invention.

Heterocyclic systems reported in the prior art are often either too stable or too unstable and are therefore rather unsuitable as delivery systems for the controlled release of volatiles in practical applications. It is therefore necessary to reach an optimal balance between stability and unstability so as to obtain a release rate of the precursors as required for the different applications, a task which is very difficult to achieve. WO 02/38120, for example, describes photolabile precursors of oxazolidines, presumably to increase the stability of the oxazolidine moiety against hydrolysis. Nevertheless, photolabile delivery systems are often not ideal for practical applications, as their release rates depend on the light-intensity to which the precursor is exposed. Therefore, there is still a need to develop new delivery systems that are sufficient stable against hydrolysis during product storage and which release the active substance by hydrolysis without relying on additional release triggers such as light or enzymes.

DESCRIPTION OF THE INVENTION

Surprisingly, we have now found 3- to 7-membered 1,3-diaza-4-oxo-heterocyclic derivatives are sufficiently stable against acidic hydrolysis but allow an efficient release of bioactive aldehydes or ketones in applications. The compounds of the present invention thus increase the long-lastingness of a biologically active aldehyde or ketone in applications by providing a controlled release system of these active compounds.

By the term "active" we mean here that the aldehyde or ketone to which it is referred is capable of bringing a benefit or effect into its surrounding environment, and in particular a perfuming, flavoring, masking, pharmaceutical, agrochemical, insect repellent or attractant, bactericide, insecticide and/or fungicide effect. Therefore, for example, said "active aldehyde or ketone" possesses at least one property which renders it useful as perfuming or flavoring ingredient, as insect repellent or attractant or as pharmaceutical, insecticide, bactericide or fungicide. Preferred active aldehydes or ketones are perfuming or flavoring ingredients, insect repellents or attractants, bactericides or fungicides. Particularly preferred active aldehydes or ketones are perfuming or flavoring ones.

According to all the above and below mentioned embodiments of the invention, the invention's compounds are particularly useful when the active aldehyde or ketone is a perfuming ingredient, i.e. a perfuming aldehyde or ketone. A "perfuming aldehyde or ketone" is a compound, which is of current use in the perfumery industry, i.e. a compound which is used as active ingredient in perfuming preparations or compositions in order to impart a hedonic effect. In other words, such an aldehyde or ketone, to be considered as being a perfuming one, must be recognized by a person skilled in the art of perfumery as being able to impart or modify in a positive or pleasant way the odor of a composition, and not just as having an odor. From now on we will refer to said "perfuming aldehyde or ketone" also as "perfuming compounds".

The invention is carried out exactly in the same manner, independently of the exact properties of the active aldehyde or ketone. Therefore, it is understood that, even if the invention will be further illustrated herein below with a specific reference to "perfuming compounds", the below embodiments are also applicable to other active aldehydes or ketones (i.e. it is possible to replace the expression "perfuming" with "flavoring", "insect attractant", "insect repellent", "masking", "pharmaceutical", "fungicide", "insecticide" or with "bactericide", for instance).

The compounds of the invention are 3- to 7-membered 1,3-diaza-4-oxo-heterocyclic derivatives capable of releasing in a controlled manner a biologically active aldehyde or ketone and are defined by the following formula

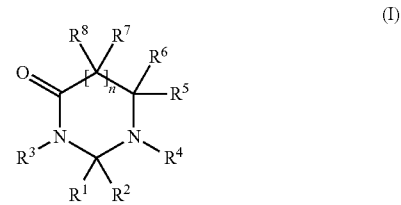

(I)

wherein
n represents an integer varying between 0 and 3;
$R^1$ and $R^2$ are the residues of an aldehyde or ketone, of formula $R^1CHO$ or $R^1R^2CO$ respectively, said aldehyde or ketone having a molecular weight comprised between 80 and 230 g/mol and having a perfuming, flavoring, masking, pharmaceutical, agrochemical, insect repellent or attractant, bactericide, insecticide and/or fungicide effect;

$R^3$ represents a hydrogen atom or a $C_1$-$C_4$ alkyl or alkenyl group optionally substituted by one group of formula $COOR^9$, $R^9$ representing a hydrogen atom or a $C_1$-$C_4$ alkyl or alkenyl group;

$R^4$ represents a hydrogen atom, or a $C_1$-$C_{12}$ alkyl, alkenyl or aryl group optionally comprising from 1 to 5 oxygen atoms;

$R^5$, $R^6$, $R^7$ and $R^8$ represent, simultaneously or independently from each other, a hydrogen atom, or a $C_1$-$C_{12}$ alkyl, alkenyl or aryl group optionally comprising from 1 to 5 oxygen atoms and/or one sulphur atom and/or one, two or three nitrogen atoms; $R^4$ and $R^5$, or $R^7$ and $R^5$, taken together, may form a $C_2$-$C_6$ alkanediyl or alkenediyl group optionally comprising one oxygen atom; if n is not 0, $R^5$ and $R^6$, taken together with the carbon atom to which they are bonded, may form a carbonyl group.

According to a particular embodiment of the invention, said compound of formula (I) can be those wherein:

n represents 0 or 1;

$R^2$ represents a hydrogen atom and $R^1$ is the residue of an aldehyde of formula $R^1CHO$, said aldehyde having a molecular weight comprised between 80 and 230 g/mol and having a perfuming, flavoring, masking, pharmaceutical, agrochemical, insect repellent or attractant, bactericide, insecticide and/or fungicide effect;

$R^3$ represents a hydrogen atom or a $C_1$-$C_4$ alkyl group;

$R^4$ represents a hydrogen atom, or a $C_1$-$C_4$ alkyl group optionally comprising one or two oxygen atoms;

$R^5$ and $R^6$ represent, simultaneously or independently from each other, a hydrogen atom, or a $C_1$-$C_{10}$ alkyl, alkenyl or aryl group, optionally comprising from 1 to 5 oxygen atoms and/or one sulphur atom and/or one, two or three nitrogen atoms; $R^4$ and $R^5$, taken together, may form a $C_3$-$C_4$ alkanediyl group optionally comprising one oxygen atom;

$R^7$ and $R^8$ represent, simultaneously or independently from each other, a hydrogen atom, or a $C_1$-$C_4$ alkyl group optionally comprising one or two oxygen atoms; $R^7$ and $R^5$, taken together, may form a $C_3$-$C_4$ alkanediyl group optionally comprising one oxygen atom.

It is understood when, herein above or herein below, a group is defined as being "alkyl, alkenyl or aryl group" it is meant that said group can be in the form of a linear, branched or cyclic alkyl or alkenyl group, in the form of an aryl group optionally substituted with alkyl or alkenyl groups or also in the form of a mixture of said type of groups, e.g. a specific group may comprise a linear alkyl, a branched alkenyl, a (poly)cyclic alkyl and an aryl moiety, unless a specific limitation to only one type is mentioned.

According to any of the embodiments, the compound of formula (I) is advantageously characterized by a vapor pressure below 0.01 Pa, as obtained by calculation using the software EPIwin v. 3.10 (2000, available at the US Environmental Protection Agency). According to a preferred embodiment, said vapour pressure is below 0.001 Pa.

According to a particular embodiment of the invention, n may represent 0. In such a case the invention's compounds are imidazolidinone derivatives.

As mentioned above the compound of the invention is capable of releasing a biologically active aldehyde or ketone (of formula $R^1CHO$ or $R^1R^2CO$ respectively) having specific molecular weight. According to a particular embodiment of the invention, said biologically active aldehyde or ketone, comprises between 6 or 7 and 15 carbon atoms.

Furthermore, according to any of the embodiments, said perfuming aldehyde or ketone is advantageously characterized by a vapor pressure above 2.0 Pa, as obtained by calculation using the software EPIwin v. 3.10 (2000, available at the US Environmental Protection Agency). According to another embodiment, said vapor pressure is above 5.0, or even above 7.0 Pa.

In an even more preferred embodiment, said active aldehydes of formula $R^1CHO$ are selected from the group of aldehydes of formula $R^1CHO$, wherein $R^1$ is a linear or α-branched alkyl group of $C_6$ to $C_{12}$, benzaldehyde, 1,3-benzodioxol-5-carboxaldehyde (heliotropine), 3-(1,3-benzodioxol-5-yl)-2-methylpropanal, 2,4-decadienal, 2-decenal, 4-decenal, 8-decenal, 9-decenal, 3-(6,6-dimethyl-bicyclo[3.1.1]hept-2-en-2-yl)propanal, 2,4-dimethyl-3-cyclohexene-1-carbaldehyde (Triplal®, origin: International Flavors & Fragrances, New York, USA), 3,5-dimethyl-3-cyclohexene-1-carbaldehyde, 1-(3,3-dimethyl-1-cyclohexyl)-1-ethanone, 5,9-dimethyl-4,8-decadienal, 2,6-dimethyl-5-heptenal (melonal), 3,7-dimethyl-2,6-octadienal (citral), 3,7-dimethyloctanal, 3,7-dimethyl-6-octenal (citronellal), (3,7-dimethyl-6-octenyl)acetaldehyde, 3-dodecenal, 4-dodecenal, 3-ethoxy-4-hydroxybenzaldehyde (ethyl vanillin), 4-ethyl benzaldehyde, 3-(2 and 4-ethylphenyl)-2,2-dimethylpropanal, 2-furancarbaldehyde (furfural), 2,4-heptadienal, 4-heptenal, 2-hexyl-3-phenyl-2-propenal (hexylcinnamic aldehyde), 2-hydroxybenzaldehyde, 7-hydroxy-3,7-dimethyloctanal (hydroxycitronellal), 4-hydroxy-3-methoxybenzaldehyde (vanillin), 4- and 3-(4-hydroxy-4-methylpentyl)-3-cyclohexene-1-carbaldehyde (Lyral®, origin: International Flavors and Fragrances, New York, USA), 4-isopropylbenzaldehyde (cuminaldehyde), 3-(4-isopropylphenyl)-2-methylpropanal, 2-(4-isopropylphenyl)propanal, (4R)-1-p-menthene-9-carbaldehyde (Liminal®, origin: Firmenich SA, Geneva, Switzerland), 2- and 4-methoxybenzaldehyde (anis aldehyde), 6-methoxy-2,6-dimethylheptanal (methoxymelonal), 8(9)-methoxy-tricyclo[5.2.1.0.(2,6)]decane-3(4)-carbaldehyde (Scentenal®, origin: Firmenich SA, Geneva, Switzerland), 4-methylbenzaldehyde, 2-(4-methylenecyclohexyl)propanal, 1-methyl-4-(4-methyl-3-pentenyl)-3-cyclohexen-1-carbaldehyde (Precyclemone® B, origin: International Flavors & Fragrances, New York, USA), 4-(4-methyl-3-pentenyl)-3-cyclohexene-1-carbaldehyde (Acropal®, origin: Givaudan-Roure SA., Vernier, Switzerland), (4-methylphenoxy)acetaldehyde, (4-methylphenyl)acetaldehyde, 3-methyl-5-phenylpentanal, 2-(1-methylpropyl)-1-cyclohexanone, 2,4-nonadienal, 2,6-nonadienal, 2-nonenal, 6-nonenal, 8-nonenal, 2-octenal, phenoxyacetaldehyde, phenylacetaldehyde, 3-phenylbutanal (Trifernal®, origin: Firmenich SA, Geneva, Switzerland), 3-phenylpropanal, 2-phenylpropanal (hydratropaldehyde), 3-phenyl-2-propenal (cinnamic aldehyde), 3-(4-tert-butylphenyl)-2-methylpropanal (Lilial®, origin: Givaudan-Roure SA, Vernier, Switzerland), 3-(4-tert-butylphenyl)propanal (Bourgeonal®, origin: Quest International, Naarden, Netherlands), tricyclo[5.2.1.0(2,6)]decane-4-carbaldehyde, exo-tricyclo[5.2.1.0(2,6)]decane-8exo-carbaldehyde (Vertral®, origin: Symrise, Holzminden, Germany), 2,6,6-trimethyl-bicyclo[3.1.1]heptane-3-carbaldehyde (formyl pinane), 2,4,6- and 3,5,6-trimethyl-3-cyclohexene-1-carbaldehyde, 2,2,3-trimethyl-3-cyclopentene-1-acetaldehyde (campholenic aldehyde), 2,6,10-trimethyl-2,6,9,11-dodecatetraenal, 2,5,6-trimethyl-4-heptenal, 3,5,5-trimethylhexanal, 2,6,10-trimethyl-9-undecenal, 2-undecenal, 10-undecenal or 9-undecenal and their mixtures such as Intreleven aldehyde (origin: International Flavors & Fragrances, New York, USA); wherein the underlined compounds represent, in an even more preferred embodiment of the invention, particularly useful fragrance aldehydes.

Respectively, said active ketone of formula $R^1R^2CO$ is preferably selected from the group of $C_6$-$C_{11}$ ketones of formula $R^1R^2CO$ wherein $R^1$ and $R^2$ are linear alkyl groups, damascenones and damascones, ionones and methyl ionones (such as Iralia® Total, origin: Firmenich SA, Geneva, Switzerland), irones, macrocyclic ketones such as, for example, cyclopentadecanone (Exaltone®) or 3-methyl-4-cyclopentadecen-1-one and 3-methyl-5-cyclopentadecen-1-one (Delta Muscenone) or 3-methyl-1-cyclopentadecanone (Muscone) all from Firmenich SA, Geneva, Switzerland, 1-(2-aminophenyl)-1-ethanone, 1-(5,5-dimethyl-1-cyclohexen-1-yl)-4-penten-1-one (Neobutenone®, origin: Firmenich SA, Geneva, Switzerland), 1-(3,3-dimethyl-1-cyclohexyl)-1-ethanone, 2,5-dimethyl-2-octene-6-one, 4,7-dimethyl-6-octene-3-one, (3,7-dimethyl-6-octenyloxy)acetaldehyde, 1-(2,4-dimethylphenyl)-1-ethanone, 4-(1,1-dimethylpropyl)-1-cyclohexanone (Orivone®, origin: International Flavors & Fragrances, New York, USA), 2,4-di-tert-butyl-1-cyclohexanone, ethyl 4-oxopentanoate, 1-(4-ethylphenyl)-1-ethanone, 2-hexyl-1-cyclopentanone, 2-hydroxy-3-methyl-2-cyclopenten-1-one, 4-(4-hydroxy-1-phenyl)-2-butanone (raspberry ketone), 1-(2- and 4-hydroxyphenyl)-1-ethanone, 4-isopropyl-2-cyclohexen-1-one, 1-(4-isopropyl-1-phenyl)-1-ethanone, 1(6),8-p-menthadien-2-one (carvone), 4(8)-p-menthen-3-one, 1-(1-p-menthen-2-yl)-1-propanone, menthone, (1R,4R)-8-mercapto-3-p-menthanone, 1-(4-methoxyphenyl)-1-ethanone, 7-methyl-2H,4H-1,5-benzodioxepin-3-one (Calone®), origin: C.A.L. SA, Grasse, France), 5-methyl-3-heptanone, 6-methyl-5-hepten-2-one, methyl 3-oxo-2-pentyl-1-cyclopentaneacetate (Hedione®, origin: Firmenich SA, Geneva, Switzerland), 1-(4-methylphenyl)-1-ethanone (4-methylacetophenone), 5-methyl-exo-tricyclo[6.2.1.0(2,7)]undecan-4-one, 3-methyl-4-(1,2,2-trimethylpropyl)-4-penten-2-one, 2-naphthalenyl-1-ethanone, 1-(octahydro-2,3,8,8-tetramethyl-2-naphthalenyl)-1-ethanone (isomeric mixture, Iso E Super®, origin: International Flavors & Fragrances, New York, USA), 3,4,5,6,6-pentamethyl-3-hepten-2-one, 2-pentyl-1-cyclopentanone (Delphone, origin: Firmenich SA, Geneva, Switzerland), 4-phenyl-2-butanone (benzylacetone), 1-phenyl-1-ethanone (acetophenone), 2- and 4-tert-butyl-1-cyclohexanone, 1-(4-tert-butylphenyl)-1-ethanone), 2,4,4,7-tetramethyl-6-octen-3-one, 1,7,7-trimethyl-bicyclo[2.2.1] heptan-2-one (camphor), 2,6,6-trimethyl-1-cycloheptanone, 2,6,6-trimethyl-2-cyclohexene-1,4-dione, 4-(2,6,6-trimethyl-2-cyclohexen-1-yl)-2-butanone (dihydroionone), 1-(2,4,4-trimethyl-2-cyclohexen-1-yl)-2-buten-1-one, 1-(3,5,6-trimethyl-3-cyclohexen-1-yl)-1-ethanone, 2,2,5-trimethyl-5-pentyl-1-cyclopentanone; wherein the underlined compounds represent, in an even more preferred embodiment of the invention, particularly useful fragrance ketones.

According to a particular embodiment of the invention, $R^3$ is a hydrogen atom or a methyl group. According to a particular embodiment of the invention, $R^4$ is a hydrogen atom.

According to a particular embodiment of the invention, $R^6$ is a hydrogen atom.

According to a particular embodiment of the invention, $R^5$ is a residue derived from an amino acid of formula $R^5CH(NH_2)COOH$, and in particular of a natural α-amino acid such as alanine, arginine, asparagine, cysteine, glutamate, glutamine, glycine, histidine, isoleucine, leucine, lysine, methionine, phenylalanine, proline, serine, threonine, tryptophane, tyrosine, valine, and aspartic acid, glutamic acid or of an artificial α-amino acid selected from the group of norleucine, 2-phenylglycine, isoasparagine and isoglutamine. Preferably said residue is derived from glycine, from R-cysteine or from any other amino acid having a S configuration. More preferably, said residue is derived from glycine or S-proline.

A further aspect of the invention relates to a process for preparing a compound of formula (I) characterized in that it comprises the step of reacting an active aldehyde of formula $R^1CHO$ or an active ketone of formula $R^1R^2CO$ as defined above with an aminoalkylamide derivative of formula (II),

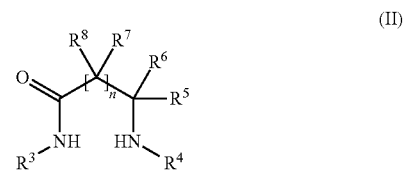

or with a hydrochloride or hydrobromide salt derived from an aminoalkylamide derivative of formula (II), $R^3$ to $R^8$ and n having the same meaning as in formula (I).

According to a particular embodiment the aminoalkylamide derivative used for the synthesis is an aminoacetamide derived from an α-amino acid. This aminoacetamide is preferably selected from the group of alaninamide, argininamide, cysteinamide, glutaminamide, glycinamide, histidinamide, leucinamide, isoleucinamide, norleucinamide, lysinamide, methioninamide, phenylalaninamide, 2-phenylglycinamide, prolinamide, serinamide, threoninamide, tryptophanamide, tyrosinamide, valinamide, isoasparaginamide, isoglutaminamide and amide of aspartic acid or glutamic acid, with glycinamide and prolinamide being particularly preferred. Several aminoacetamide derivatives are commercially available.

In particular cysteinamide has a R configuration and all other aminoacetamides have a S configuration, as the natural amino acid from which they are derived. So, the 3- to 7-membered 1,3-diaza-4-oxo-heterocyclic derivatives of the invention, which are derived from natural amino acids, are expected to have a good biocompatibility. The same is true for their degradation products. Therefore, said compound of formula (I) may constitute a particularly interesting new precursor for the controlled release of active aldehydes or ketones.

Owing to their particular chemical structure, the invention's compounds are capable of releasing, via a decomposition reaction, a residue and a biologically active ketone or aldehyde. The decomposition reaction, which leads to the release of the perfuming compounds, is believed to be influenced by pH changes or by heat, but may also be triggered by other types of mechanisms.

As mentioned above, the invention concerns the use of the above-described compounds of formula (I) for the controlled release of a perfuming ingredient. In other words it concerns a method to confer, enhance, improve or modify the odor properties of a perfuming composition or of a perfumed article by the controlled release of a perfuming aldehyde or ketone, which method comprises adding to said composition or article an effective amount of at least an invention's compound. By "use of an invention's compound" it has to be understood here also the use of any composition containing said compounds and which can be advantageously employed in perfumery industry as active ingredients.

Said compositions, which in fact can be advantageously employed as perfuming ingredient, are also an object of the present invention.

Therefore, another object of the present invention is a perfuming composition comprising:

i) as perfuming ingredient, at least one of the invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

Generally speaking, by "perfumery base" we mean here a composition comprising at least one perfuming co-ingredient.

Said perfuming co-ingredient is not a compound according to the invention. Moreover, by "perfuming co-ingredient" it is meant here a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

Generally speaking, by "perfumery adjuvant" we mean here an ingredient capable of imparting additional added benefit such as a color, a particular light resistance, chemical stability and etc. A detailed description of the nature and type of adjuvant commonly used in perfuming bases cannot be exhaustive, but it has to be mentioned that said ingredients are well known to a person skilled in the art.

An invention's composition consisting of at least one of the invention's compounds and at least one perfumery carrier represents a particular embodiment of the invention as well as a perfuming composition comprising at least one of the invention's compounds, at least one perfumery carrier, at least one perfumery base, and optionally at least one perfumery adjuvant.

It is useful to mention here that the possibility to have, in the compositions mentioned above, more than one of the invention's compounds or other precursors of similar type is important as it enables the perfumer to prepare accords, perfumes, possessing the odor tonality of various compounds of the invention, creating thus new tools for their work.

Furthermore, an invention's compound, or a perfuming composition comprising it, is a useful perfuming ingredient, which can be advantageously used in all the fields of modern perfumery, such as fine perfumery or functional perfumery. Indeed, the invention's compounds may be advantageously employed in fine or functional perfumery to achieve a more controlled deposition, and consequent release, of perfuming compounds. For example, the compounds according to the invention, owing to a good substantivity, a low volatility and a well controlled release of odoriferous molecules, can be incorporated in any application requiring the effect of rapid or prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin. Consequently, a perfumed article comprising:

i) as perfuming ingredient, at least one of the invention's compounds as defined above; and
ii) a consumer product base;

is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactively effective amount of at least one of the invention's compounds.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, creams, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

In particular, we have found that the invention's compounds are particularly well suited for articles having an acidic pH, such as comprised, e.g., between 2.5 and 7.

Some of the above-mentioned consumer product bases may represent an aggressive medium for the invention's compounds, so that it may be necessary to protect the latter from premature decomposition, for example by encapsulation.

Preferred perfuming compositions or perfumed articles are perfumes, fabric detergents or softener bases.

Typical examples of fabric detergents or softener composition into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the compounds according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 10% by weight, or even more, of the compounds of the invention based on the weight of the composition into which they are incorporated. Concentrations lower than these, such as in the order of 0.001% to 5% by weight, can be used when these compounds are applied directly in the perfuming of the various consumer products mentioned hereinabove.

Another object of the present invention relates to a method for the perfuming of a surface or to a method for intensifying or prolonging the diffusion effect of the characteristic fragrance of an odoriferous ingredient on a surface, characterized in that said surface is treated in the presence of an invention's compound. Suitable surfaces are, in particular, textiles, hard surfaces, hair and skin.

EXAMPLES

The invention will now be described in further detail by way of the following examples, wherein the abbreviations have the usual meaning in the art, the temperatures are indicated in degrees centigrade (° C.). High resolution electrospray mass spectra (HR-ESI-MS) were recorded on an Agilent 1200 RR high performance liquid chromatograph, equipped with an Agilent Eclipse Plus C18 column (2.1×100 mm i.d.), eluted at 0.5 ml/min with a gradient of water (containing 0.1% of formic acid)/acetonitrile at 50° C. and coupled to a MSD TOF HR G3250A mass spectrometer (multimode source, dual mode positive) at 350° C., with the $N_2$ flow at 5 ml/min, the nebulizer pressure at 40 psi, the capillary voltage at 3000 V and the fragmentor voltage at 140 V. Commercially available reagents and solvents were used without further purification if not stated otherwise. Reactions were carried out in standard glassware under $N_2$.

Although specific conformations or configurations are indicated for some of the compounds, this is not meant to limit the use of these compounds to the isomers described. According to the invention, all possible conformation or configuration isomers are expected to have a similar effect.

Example 1

Preparation of 1,3-diaza-4-oxo-heterocyclic Derivatives a) Synthesis of 2-(2-phenylpropyl)imidazolidin-4-one A mixture of 3-phenylbutanal (Trifernal®, 0.67 g, 4.5 mmol), glycinamide hydrochloride (0.50 g, 4.5 mmol), triethylamine (0.46 g, 4.5 mmol) and $K_2CO_3$ in ethanol (4 ml) was heated to 60° C. for 24 h. Then the solvent was removed under vacuum at 40° C. The residue was taken up in ether and the solvent evaporated to yield 0.52 g (57%) of a highly viscous oil as a mixture of diastereoisomers.

HR-ESI-MS (pos.): 205.1333 $[M+H]^+$; $C_{12}H_{17}N_2O^+$, calc.: 205.1340.

b) Synthesis of (±)-(7aS)-3-(2-phenylpropyl)hexahydro-1H-pyrrolo[1,2-C]imidazol-1-one A mixture of Trifernal® (0.65 g, 4.4 mmol), S-prolinamide (0.50 g, 4.4 mmol) and $K_2CO_3$ in ethanol (4.48 g) was heated to 60° C. for 24 h. Then the solvent was removed under vacuum at 40° C. The residue was taken up in ether and the solvent evaporated to yield 1.03 g (97%) of an oil as a mixture of diastereoisomers.

HR-ESI-MS (pos.): 245.1658 $[M+H]^+$; $C_{15}H_{21}N_2O^+$, calc.: 245.1653.

c) Synthesis of (5S)-5-methyl-2-(2-phenylpropyl) imidazolidin-4-one

A mixture of 3-phenylbutanal (Trifernal®, 1.18 g, 8.0 mmol), S-alaninamide hydrochloride (1.00 g, 8.0 mmol), triethylamine (0.81 g, 8.0 mmol) and $K_2CO_3$ (0.98 g) in ethanol (8 ml) was heated to 60° C. for 24 h. Then the solvent was removed under vacuum at 40° C. The residue was taken up in ether, filtered and the filtrate concentrated. Drying under vacuum yielded 1.87 g (quant.) of an oil as a mixture of diastereoisomers.

HR-ESI-MS (pos.): 219.1488 $[M+H]^+$; $C_{13}H_{19}N_2O^+$, calc.: 219.1497.

d) Synthesis of (5S)-5-benzyl-2-(2-phenylpropyl) imidazolidin-4-one

A mixture of Trifernal® (0.74 g, 5.0 mmol), S-phenylalaninamide hydrochloride (1.00 g, 8.0 mmol), triethylamine (0.51 g, 5.0 mmol) and $K_2CO_3$ (0.98 g) in ethanol (8 ml) was heated to 60° C. for 24 h. Then the solvent was removed under vacuum at 40° C. and the residue dried under vacuum to yield 1.41 g (96%) of a solid as a mixture of diastereoisomers.

HR-ESI-MS (pos.): 295.1804 $[M+H]^+$; $C_{19}H_{23}N_2O^+$, calc.: 295.1810.

e) Synthesis of (5S)-5-benzyl-2-nonylimidazolidin-4-one

A mixture of decanal (0.78 g, 5.0 mmol), S-phenylalaninamide hydrochloride (1.00 g, 5.0 mmol), triethylamine (0.51 g, 5.0 mmol) and $K_2CO_3$ (1.00 g) in ethanol (8 ml) was heated to 60° C. for 24 h. Then the solvent was removed under vacuum at 40° C. The residue was taken up in ether, filtered and concentrated to yield 1.67 g (quant.) of an oil as a mixture of diastereoisomers.

HR-ESI-MS (pos.): 303.2408 $[M+H]^+$; $C_{19}H_{31}N_2O^+$, calc.: 303.2436.

f) Synthesis of (5S)-5-isobutyl-2-(2-phenylpropyl) imidazolidin-4-one

A mixture of Trifernal® (0.89 g, 6.0 mmol), S-leucinamide hydrochloride (1.00 g, 6.0 mmol), triethylamine (0.61 g, 6.0 mmol) and $K_2CO_3$ (ca. 1 g) in ethanol (8 ml) was heated to 60° C. for 24 h. Then the solvent was removed under vacuum at 40° C. The residue was taken up in ether, filtered and concentrated to yield 1.70 g (quant.) of an oil as a mixture of diastereoisomers.

g) Synthesis of (5S)-5-isobutyl-2-(2,4,4-trimethyl-pentyl)imidazolidin-4-one A mixture of 3,5,5-trimethylhexanal (3.06 g, 21.5 mmol), S-leucinamide hydrochloride (3.00 g, 18.0 mmol) and triethylamine (1.78 g, 18.0 mmol) in dichloromethane (25 ml) was heated at reflux for 16 h using an inverse water separator. Then the solution was cooled to 0° C. and trifluoroacetic acid (3.09 g, 27.1 mmol) was added dropwise. After warming to room temperature, the mixture was left stirring for 5 h. The obtained suspension was basified (pH ca. 11) with KOH (2 N, 20 ml). The mixture was extracted with dichloromethane (5×) and the organic phases dried ($Na_2SO_4$) and concentrated. The remaining volatiles were removed by Kugelrohr distillation to give 5.71 g (quant.) of an oil as a mixture of diastereoisomers.

HR-ESI-MS (pos.): 255.2457 $[M+H]^+$; $C_{15}H_{31}N_2O^+$, calc.: 255.2436.

Example 2

Stability of 1,3-diaza-4-oxo-heterocyclic Derivatives Against Acidic Hydrolysis The stability of the 3- to 7-membered 1,3-diaza-4-oxo-heterocyclic derivatives according to the invention against acidic hydrolysis was tested by NMR-spectroscopy in a phosphate buffer solution (in $D_2O/CD_3OD$ 1:1).

For the measurements, an acidic deuterated phosphate buffer stock solution was prepared from 2.07 g of orthophosphoric acid (origin: Fluka), 1.46 g of monobasic $KH_2PO_4$ (origin: Acros) and 77.36 g (=70 ml, $D_{20°\,C.}$=1.105 g/ml) of deuterium oxide. To determine the pH of the final reaction solution, 0.5 ml of the buffer stock solution were diluted with 0.5 ml of $CD_3OD$ to give a final mixture of $D_2O/CD_3OD$ 1:1 (v/v). The pH of this solution was measured to be 2.75 at 26.4° C., and the corresponding pD value was calculated with the formula $pD=pH_{measured}+0.33$ to be 3.08.

10 mM product solutions were then prepared by adding 0.35 ml of $CD_3OD$ and 0.1 ml of 2-(2-phenylpropyl)imidazolidin-4-one (11.0 mg in 0.3 ml of $CD_3OD$) or 0.1 ml of (±)-(7aS)-3-(2-phenylpropyl)hexahydro-1H-pyrrolo[1,2-C] imidazol-1-one (8.8 mg in 0.4 ml of $CD_3OD$), respectively, to 0.45 ml of the above described phosphate buffer stock solution. $^1$H-NMR spectra of these solutions were recorded after 2 and 5 days on a Bruker AV 500 spectrometer at 500 MHz. No hydrolysis of the precursors was observed under these conditions.

Example 3

Performance of a Fabric Softener Base Comprising 1,3-diaza-4-oxo-heterocyclic Derivatives The controlled release effect of the compounds of formula (I) is evidenced by headspace analysis on dry fabric one and three days after treatment with a fabric softener comprising this compound. Higher amounts of free aldehydes and ketones are detected in the samples treated with the compounds of the invention as compared to the corresponding reference sample with the free fragrance aldehyde or ketone. The tests have been performed in the following way.

A fabric softener base (pH ca. 3.14) was prepared with the following ingredients:

| | |
|---|---|
| Stepantex ® VK90 (origin: Stepan) | 16.5% (w/w), |
| Calcium chloride | 0.2% (w/w), |
| Water | 83.3% (w/w). |

The release over time of active aldehydes/ketones from the compounds of the invention as compared to the corresponding unmodified free aldehyde/ketone was determined in the following experiments:

In a 1 l beaker, 1 ml of a solution of 2-(2-phenylpropyl) imidazolidin-4-one (A, 36.0 mg in 2 ml of ethanol) or (±)-(7aS)-3-(2-phenylpropyl)hexahydro-1H-pyrrolo[1,2-C]imidazol-1-one (B, 36.1 mg in 2 ml of ethanol), respectively, were added to 1.80 g of the homogenized fabric softener base and filled up with 600 g of demineralized cold tap water. Two cotton sheets (EMPA cotton test cloth Nr. 221, origin: Eidgenössische Materialprüfanstalt (EMPA)), pre-washed with an unperfumed detergent powder and cut to ca. 12×12 cm sheets) were added to each beaker and agitated manually for 3 min, left standing for 2 min, then wrung out by hand and weighed to estimate the quantity of residual water. As a reference sample, 1 ml of a solution containing an equimolar amount of unmodified Trifernal® (65.3 mg and 54.7 mg in 5 ml of ethanol for A and B, respectively) was added to another 1.80 g of the original fabric softener base which was treated as described above. All cotton sheets were line-dried for 1 or 3 days, respectively. One of the dry cotton sheets was put into a headspace sampling cell (internal volume ca. 160 ml), thermostatted at 25° C. and exposed to a constant air flow of ca. 200 ml/min, respectively. The air was filtered through active charcoal and aspirated through a saturated solution of NaCl, corresponding to a constant humidity of ca. 75%. During 15 min the volatiles were adsorbed onto a waste Tenax® cartridge, then during 15 min on a clean Tenax® cartridge. The sampling was repeated 7 times every 60 min (45 min trapping on the waste cartridge and 15 min on a clean cartridge). All experiments were carried out in duplicate. The cartridges were desorbed on a Perkin Elmer TurboMatrix ATD desorber coupled to a Carlo Erba MFC 500 gas chromatograph equipped with a J&W Scientific DB1 capillary column (30 m, i.d. 0.45 mm, film 0.42 mm) and a FID detector. The volatiles were analyzed using a two steps temperature gradient starting from 70° C. to 130° C. at 3° C./min and then going to 260° C. at 25° C./min. The injection temperature was at 240° C., the detector temperature at 260° C. Headspace concentrations (in ng/l) were obtained by external standard calibrations using five different concentrations of the aldehyde in ethanol. 2 ml of each calibration solution were injected with a microliter syringe onto three clean Tenax® cartridges, respectively. All the cartridges were desorbed immediately under the same conditions as those resulting from the headspace sampling. The following average amounts of aldehydes were detected on dry fabric from the sample containing compound of the invention as compared to the free reference aldehyde (in brackets) after 1 and 3 days:

| Time [min] | Amount of aldehyde released from A | | Amount of aldehyde released from B | |
|---|---|---|---|---|
| | after 1 d [ng/l] | after 3 d [ng/l] | after 1 d [ng/l] | after 3 d [ng/l] |
| 30 | 10.8 (5.7) | 6.2 (1.5) | 2.2 (3.1) | 3.4 (1.3) |
| 90 | 38.9 (11.6) | 24.9 (4.0) | 8.9 (5.0) | 17.7 (2.6) |
| 150 | 51.9 (13.5) | 33.6 (6.1) | 12.7 (10.1) | 28.3 (8.0) |

-continued

| Time [min] | Amount of aldehyde released from A | | Amount of aldehyde released from B | |
|---|---|---|---|---|
| | after 1 d [ng/l] | after 3 d [ng/l] | after 1 d [ng/l] | after 3 d [ng/l] |
| 210 | 53.7 (16.0) | 36.6 (8.2) | 14.9 (8.2) | 27.7 (3.4) |
| 270 | 52.7 (16.0) | 37.7 (8.4) | 15.0 (8.8) | 27.0 (3.8) |
| 330 | 50.6 (15.6) | 37.1 (7.2) | 14.5 (9.3) | 25.3 (4.3) |
| 390 | 49.0 (14.6) | 33.7 (6.6) | 15.3 (9.7) | 23.0 (4.0) |
| 450 | 46.2 (13.7) | 35.1 (5.6) | 14.4 (10.0) | 22.1 (4.3) |

The data show that higher amounts of the corresponding aldehyde were released into the headspace from the invention's compound as compared to the free active compound. Despite their inherent stability against hydrolysis in an aqueous buffer solution (see Example 2), 2-(2-phenylpropyl)imidazolidin-4-one and (±)-(7aS)-3-(2-phenylpropyl) hexahydro-1H-pyrrolo[1,2-C]imidazol-1-one surprisingly release the desired active aldehydes or ketones at suitable rates in practical applications. In contrast to many prior-art precursors, the compounds according to the present invention seem to represent an ideal compromise between sufficient product stability against acidic hydrolysis and efficient release rate upon hydrolysis in practical applications.

The invention claimed is:

1. A compound of formula (I),

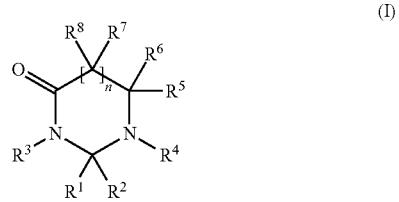

(I)

wherein:
n represents 0;
$R^1$ and $R^2$ are the residues of an aldehyde or ketone of formula $R^1CHO$ or $R^1R^2CO$ respectively, said aldehyde or ketone having a molecular weight comprised between 80 and 230 g/mol, between 7 and 15 carbon atoms, and a perfuming or flavoring effect;
$R^3$ represents a hydrogen atom or a $C_1$-$C_4$ alkyl or alkenyl group optionally substituted by one group of formula $COOR^9$, $R^9$ representing a hydrogen atom or a $C_1$-$C_4$ alkyl or alkenyl group;
$R^4$ represents a hydrogen atom, or a $C_1$-$C_{12}$ alkyl, alkenyl or aryl group optionally comprising from 1 to 5 oxygen atoms;
$R^5$, $R^6$, $R^7$ and $R^8$ represent, simultaneously or independently from each other, a hydrogen atom, or a $C_1$-$C_{12}$ alkyl, alkenyl or aryl group, optionally comprising from 1 to 5 oxygen atoms, one sulphur atom, or one, two or three nitrogen atoms; $R^4$ and $R^5$, or $R^7$ and $R^5$, taken together, may form a $C_2$-$C_6$ alkanediyl or alkenediyl group optionally comprising one oxygen atom.

2. A compound according to claim 1, wherein:
n represents 0;
$R^2$ represents a hydrogen atom and $R^1$ is the residue of an aldehyde of formula $R^1CHO$, said aldehyde having a molecular weight comprised between 80 and 230 g/mol, between 7 and 15 carbon atoms, and a perfuming or flavoring effect;
$R^3$ represents a hydrogen atom or a $C_1$-$C_4$ alkyl group;
$R^4$ represents a hydrogen atom, or a $C_1$-$C_4$ alkyl group optionally comprising one or two oxygen atoms;
$R^5$ and $R^6$ represent, simultaneously or independently from each other, a hydrogen atom, or a $C_1$-$C_{10}$ alkyl, alkenyl or aryl group optionally comprising from 1 to 5 oxygen atoms and/or one sulphur atom and/or one, two or three nitrogen atoms; $R^4$ and $R^5$, taken together, may form a $C_3$-$C_4$ alkanediyl group optionally comprising one oxygen atom;
$R^7$ and $R^8$ represent, simultaneously or independently from each other, a hydrogen atom, or a $C_1$-$C_4$ alkyl group optionally comprising one or two oxygen atoms; $R^7$ and $R^5$, taken together, may form a $C_3$-$C_4$ alkanediyl group optionally comprising one oxygen atom.

3. A compound according to claim 1, wherein $R^6$ is a hydrogen atom.

4. A compound according to claim 3, wherein $R^5$ is a residue derived from an α-amino acid selected from the group consisting of as alanine, arginine, asparagine, cysteine, glutamate, glutamine, glycine, histidine, isoleucine, leucine, lysine, methionine, phenylalanine, proline, serine, threonine, tryptophane, tyrosine, valine, and aspartic acid, glutamic acid or of an artificial α-amino acid selected from the group of norleucine, 2-phenylglycine, isoasparagine and isoglutamine.

5. A compound according to claim 3, wherein $R^5$ is a residue derived from glycine or S-proline.

6. A compound of formula (I),

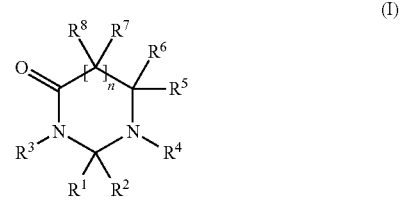

(I)

wherein:
n represents 0;
$R^1$ and $R^2$ are the residues of an aldehyde or ketone of formula $R^1CHO$ or $R^1R^2CO$ respectively, said aldehyde or ketone having a molecular weight comprised between 80 and 230 g/mol and a perfuming, flavoring, masking, pharmaceutical, agrochemical, insect repellent or attractant, bactericide, insecticide and/or fungicide effect;
$R^3$ represents a hydrogen atom or a $C_1$-$C_4$ alkyl or alkenyl group optionally substituted by one group of formula $COOR^9$, $R^9$ representing a hydrogen atom or a $C_1$-$C_4$ alkyl or alkenyl group;
$R^4$ represents a hydrogen atom, or a $C_1$-$C_{12}$ alkyl, alkenyl or aryl group optionally comprising from 1 to 5 oxygen atoms;
$R^5$, $R^7$ and $R^8$ represent, simultaneously or independently from each other, a hydrogen atom, or a $C_1$-$C_{12}$ alkyl, alkenyl or aryl group, optionally comprising from 1 to 5 oxygen atoms, one sulphur atom, or one, two or three nitrogen atoms; $R^4$ and $R^5$, or $R^7$ and $R^5$, taken together, may form a $C_2$-$C_6$ alkanediyl or alkenediyl group optionally comprising one oxygen atom;
wherein $R^5$ is a residue derived from an α-amino acid selected from the group consisting of as alanine, arginine, asparagine, cysteine, glutamate, glutamine, glycine, histidine, isoleucine, leucine, lysine, methionine, phenylalanine, proline, serine, threonine, tryptophane, tyrosine, valine, and aspartic acid, glutamic acid or of an artificial α-amino acid selected from the group of norleucine, 2-phenylglycine, isoasparagine and isoglutamine; and $R^6$ represents a hydrogen atom.

7. A compound according to claim 6, wherein $R^5$ is a residue derived from glycine or S-proline.

8. A compound of formula (I),

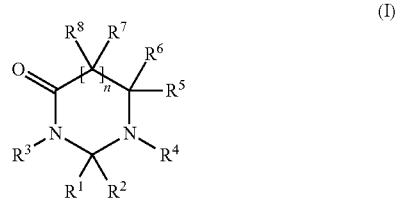

(I)

wherein:

n represents 0;

$R^1$ and $R^2$ are the residues of an aldehyde or ketone of formula $R^1$CHO or $R^1R^2$CO respectively, said aldehyde or ketone having a molecular weight comprised between 80 and 230 g/mol and a perfuming, flavoring, masking, pharmaceutical, agrochemical, insect repellent or attractant, bactericide, insecticide and/or fungicide effect;

$R^3$ represents a hydrogen atom or a $C_1$-$C_4$ alkyl or alkenyl group optionally substituted by one group of formula COOR$^9$, $R^9$ representing a hydrogen atom or a $C_1$-$C_4$ alkyl or alkenyl group;

$R^4$ represents a hydrogen atom, or a $C_1$-$C_{12}$ alkyl, alkenyl or aryl group optionally comprising from 1 to 5 oxygen atoms;

$R^5$, $R^6$, $R^7$ and $R^8$ represent, simultaneously or independently from each other, a hydrogen atom, or a $C_1$-$C_{12}$ alkyl, alkenyl or aryl group, optionally comprising from 1 to 5 oxygen atoms, one sulphur atom, or one, two or three nitrogen atoms; $R^4$ and $R^5$, or $R^7$ and $R^5$, taken together, may form a $C_2$-$C_6$ alkanediyl or alkenediyl group optionally comprising one oxygen atom;

wherein $R^5$ is a residue derived from an α-amino acid selected from the group consisting of as alanine, arginine, asparagine, cysteine, glutamate, glutamine, glycine, histidine, isoleucine, leucine, lysine, methionine, phenylalanine, proline, serine, threonine, tryptophane, tyrosine, valine, and aspartic acid, glutamic acid or of an artificial α-amino acid selected from the group of norleucine, 2-phenylglycine, isoasparagine and isoglutamine.

9. A compound according to claim 6, wherein $R^5$ is a residue derived from glycine or S-proline.

10. A method to confer, enhance, improve or modify the odor properties of a perfuming composition or of a perfumed article by the controlled release of a perfuming aldehyde or ketone, which method comprises adding to said composition or article an effective amount of at least one compound of formula (I) according to claim 1.

11. A perfuming composition comprising:
a) as perfuming ingredient, at least one compound of formula (I) according to claim 1;
b) at least one ingredient selected from the group consisting of a perfumery carrier and a perfumery base; and
c) optionally at least one perfumery adjuvant.

12. A consumer article, comprising:
a) as active ingredient, at least one compound of formula (I) according to claim 1; and
b) a consumer product base.

13. A method to confer, enhance, improve or modify the odor properties of a perfuming composition or of a perfumed article by the controlled release of a perfuming aldehyde or ketone, which method comprises adding to said composition or article an effective amount of at least one compound of formula (I) according to claim 6.

14. A perfuming composition comprising:
a) as perfuming ingredient, at least one compound of formula (I) according to claim 6;
b) at least one ingredient selected from the group consisting of a perfumery carrier and a perfumery base; and
c) optionally at least one perfumery adjuvant.

15. A consumer article, comprising:
a) as active ingredient, at least one compound of formula (I) according to claim 6; and
b) a consumer product base.

16. A method to confer, enhance, improve or modify the odor properties of a perfuming composition or of a perfumed article by the controlled release of a perfuming aldehyde or ketone, which method comprises adding to said composition or article an effective amount of at least one compound of formula (I) according to claim 8.

17. A perfuming composition comprising:
a) as perfuming ingredient, at least one compound of formula (I) according to claim 8;
b) at least one ingredient selected from the group consisting of a perfumery carrier and a perfumery base; and
c) optionally at least one perfumery adjuvant.

18. A consumer article, comprising:
a) as active ingredient, at least one compound of formula (I) according to claim 8; and
b) a consumer product base.

* * * * *

UNITED STATES PATENT AND TRADEMARK OFFICE
CERTIFICATE OF CORRECTION

PATENT NO. : 8,399,499 B2
APPLICATION NO. : 12/598153
DATED : March 19, 2013
INVENTOR(S) : Herrmann et al.

Page 1 of 1

It is certified that error appears in the above-identified patent and that said Letters Patent is hereby corrected as shown below:

In the Claims:
Column 13:
Line 54, change "$R^3$," to -- $R^5$, --.

Signed and Sealed this
Seventh Day of May, 2013

Teresa Stanek Rea
*Acting Director of the United States Patent and Trademark Office*